United States Patent [19]
Ikuno et al.

[11] 4,102,341
[45] Jul. 25, 1978

[54] ELECTRIC KNIFE DEVICE

[75] Inventors: Yuzi Ikuno, Fuchu; Yutaka Tanaka, Hachioji, both of Japan

[73] Assignee: Olympus Optical Co., Ltd., Tokyo, Japan

[21] Appl. No.: 751,015

[22] Filed: Dec. 16, 1976

[30] Foreign Application Priority Data

Dec. 20, 1975 [JP] Japan .................. 50-152368

[51] Int. Cl.² ............................................. A61N 3/02
[52] U.S. Cl. ........................... 128/303.14; 128/303.17
[58] Field of Search .................... 128/303.14, 303.13, 128/303.17, 303.18, 2.1 P

[56] References Cited

U.S. PATENT DOCUMENTS

| 3,601,126 | 8/1971 | Estes | 128/303.14 |
| 3,634,652 | 1/1972 | Shimizu et al. | 128/303.18 X |
| 3,683,923 | 8/1972 | Anderson | 128/303.14 |
| 3,885,569 | 5/1975 | Judson | 128/303.14 |
| 3,897,787 | 8/1975 | Ikuno et al. | 128/303.14 |
| 3,923,063 | 12/1975 | Andrews et al. | 128/303.14 |

FOREIGN PATENT DOCUMENTS 2,439,587  2/1975  Fed. Rep. of Germany .... 128/2.1 P

Primary Examiner—Robert W. Michell
Assistant Examiner—Lee S. Cohen

[57] ABSTRACT

An electric knife device comprises a high frequency current source, a knife electrode, a patient electrode opposed to the knife electrode, a first wire coupling one output of the high frequency source and the knife electrode, a second wire coupling the other output of the high frequency source and the patient electrode, first and second current detectors for detecting the currents flowing through the first and second wires, respectively, a division circuit for calculating the ratio between the outputs of the first and second current detectors, the current flowing through the first wire being controlled when the ratio calculated by the division circuit becomes lower than a predetermined value.

8 Claims, 3 Drawing Figures

ELECTRIC KNIFE DEVICE

BACKGROUND OF THE INVENTION

This invention relates to an electric knife device for simultaneously cutting and searing affected tissue, using high frequency current.

An electric knife device comprises a knife electrode which serves as a knife and a patient electrode which is to be attached the patient. To remove or cut open affected tissue, the patient electrode is attached to the patient, and the knife electrode is opposed to the patient electrode with the affected tissue therebetween. This done, high frequency current is made to flow between the electrodes.

During removal or cutting of the affected tissue a good electrical contact should be maintained between the patient and the patient electrode. But if the ratio of the applied high frequency current to the contacting area between the patient electrode and the patient's skin becomes smaller than a predetermined value, or if a wire connecting the patient electrode with the high frequency current source is cut off the skin is often burnt. Such a skin burn occurs when the current density at the contacting area is about 100 mA/cm$^2$.

In order to avoid such a skin burn, use may be made of a patient electrode having a contacting surface area of about 15 cm $\times$ 15 cm. In addition, gauze impregnated with an electrically conductive liquid such as water is interposed between the patient electrode and the patient's skin. But as the operation goes on for a long time, the liquid is heated by the patient's temperature and is likely to evaporate. If this happens, the electrical contact between the patient and the patient electrode is degraded critically.

Further, if monitor electrodes of an electrocardiograph are attached to the chest of the patient or a part of the patient touches the metallic portion of the operation table, the high frequency current from the knife electrode often fail to flow to the patient electrode, flowing instead to the electrodes of the electrocardiograph or to the metallic portion of the table. If the contacting area between the skin and the monitor electrodes or the metallic portion is so small as to increase the current density more than the abovementioned 100 mA/cm$^2$, skin burn often takes place.

SUMMARY OF THE INVENTION

The object of this invention is to provide an electric knife device which is not accompanied by accidents such as skin burn due to a leak of high frequency current or due to the disconnection of the wire.

The electric knife device according to the invention comprises a high frequency current source having at least first and second output terminals, a knife electrode connected to the first output terminal, a patient electrode connected to the second output terminal and to be attached electrically to the patient, a first current detector for detecting the current flowing between the first output terminal and the knife electrode, a second current detector for detecting the current flowing between the second output terminal and the patient electrode, a division circuit for calculating the ratio between the outputs of the first and second current detectors, and means for controlling the high frequency current flowing through the knife electrode in accordance with the ratio calculated by the division circuit.

DESCRIPTION OF THE PREFERRED EMBODIMENT

Figure 1:
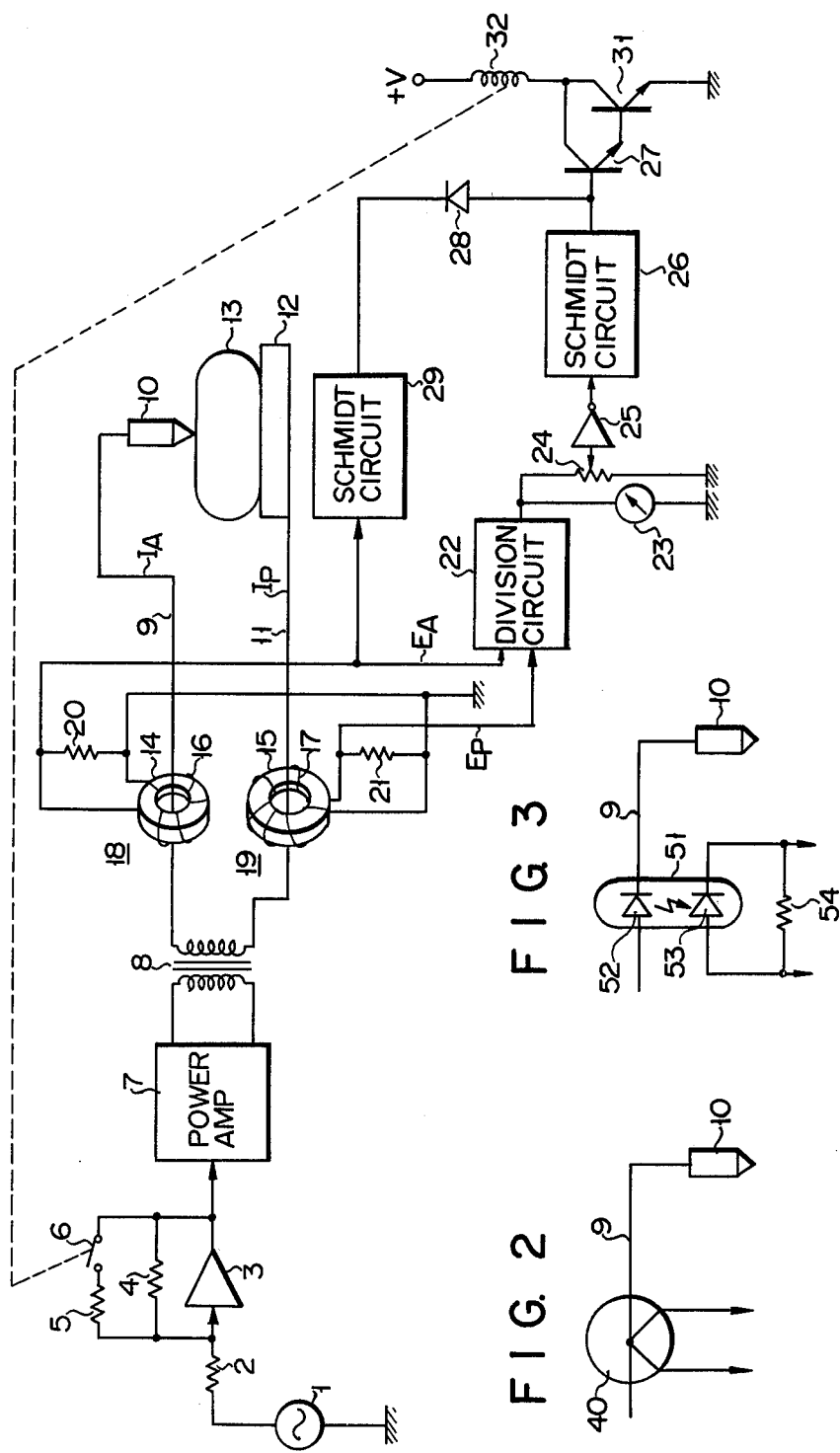
FIG. 1 shows the circuit diagram of one embodiment of the invention.

As shown in FIG. 1, an oscillator 1 for generating a high frequency of, for example, 600 kHz has its output supplied through an input resistor 2 to a voltage amplifier 3. Thus, the output of the high frequency oscillator 1 is amplified by the voltage amplifier 3. A feedback loop including a resistor 4 is constituted between the input and output terminals of the voltage amplifier 3. Connected in parallel to the resistor 4 is a serial circuit which is constituted by a resistor 5 and a normally opened relay switch 6.

The output of the voltage amplifier circuit 3 is supplied to a power amplifier 7 and is amplified there. The amplified output is then supplied to the primary winding of a transformer 8. In the secondary winding of the transformer 8 there is induced a high frequency current of 600 kHz. One terminal of the secondary winding of the transformer 8 is connected through a wire 9 to a knife electrode 10, while the other terminal of the secondary winding is connected through another wire 11 to a patient electrode 12. The patient electrode 12 is a metal plate sized, for example, 15 $\times$ 15 cm and is to be attached to a patient 13.

The wires 9 and 11 pass through toroidal-shaped cores 14 and 15, respectively. About these cores 14 and 15 there are wound coils 16 and 17 of the same number of turns, respectively. Thus, the wire 9, the core 14 and the coil 16 constitute a transformer 18. Similarly, the wire 11, the core 15 and the coil 17 constitute another transformer 19. Between the terminals of the coil 16 there is connected a resistor 20, and between the terminals of the coil 17 there is connected a resistor 21 of the same specific resistivity as the resistor 20. One terminal of the resistor 20 is connected to the divisor input terminal of a division circuit 22, while one terminal of the resistor 21 is connected to the dividend input terminal of the division circuit 22. The other terminals of the resistors 20 and 21 are connected to a zero volt common or ground.

The division circuit 22 is to calculate the ratio of the voltage $E_P$ at the terminal of the resistor 21 to the voltage $E_A$ at the terminal of the resistor 20. Its output, which represents $E_P/E_A$, is supplied to a voltmeter 23 and to one terminal of a potentiometer 24. The other terminal of the potentiometer 24 is grounded, and the sliding terminal of the same is connected to the input terminal of an analog inverter 25. The output of the analog inverter 25 is supplied to a Schmidt circuit 26. The output of the Schmidt circuit 26 is coupled to the base of a transistor 27 and the anode of a diode 28. The cathode of the diode 28 is coupled to the output side of another Schmidt circuit 29.

The input terminal of the Schmidt circuit 29 is connected to one terminal of the resistor 20. The emitter of the transistor 27 is connected to the base of a transistor 31, the emitter of which is grounded. The collectors of the transistors 27 and 31 are connected commonly to one terminal of a relay coil 32, the other terminal of which is connected to a +V power source. The relay coil 32 and the normally opened relay switch 6 form a relay. When the relay coil 32 is energized, the relay switch 6 is made to close. The transistors 27 and 31 constitute a switching circuit of Darlington connection.

The electric knife device shown in FIG. 1 is operated in the following manner.

So long as a good electrical contact is maintained between the patient electrode 12 and the patient 13, a searing current of about 0.4 A and, for instance, 600 kHz flows from the knife electrode 10 to the patient electrode 12 through the patient 13. In this case, substantially no current leak takes place, and the current flowing through the wire 9 is substantially equal to the current flowing through the wire 11. As a result, substantially the same voltage is induced at the coils 16 and 17 of the transformers 18 and 19. Thus, substantially the same voltage is applied on the corresponding terminals of the resistors 20 and 21. The voltage $E_A$ at the one terminal of the resistor 20 is fed to the divisor input terminal of the division circuit 22, while the voltage $E_P$ at the one terminal of the resistor 21 is fed to the dividend input terminal thereof.

Then, the division circuit 22 divides $E_P$ by $E_A$. Since $E_P$ is substantially equal to $E_A$, the ratio of K of $E_P$ to $E_A$ is substantially "1". Thus the division circuit 22 generates the corresponding output to $K = 1$. The voltage is indicated by the voltmeter 23. Simultaneously it is divided by the potentiometer 24, then subjected to polarity inversion at the inverter 25 and finally applied to the Schmidt circuit 26.

The Schmidt circuit 26 is so designed to produce an output when the output of the inverter 25 is higher than a predetermined level. In other words, it is triggered when the output of the division circuit 22, or the output of the potentiometer 24, is lower than the predetermined level. The predetermined level corresponds to a specific value of $E_P/E_A$ which depends on the leak current. More specifically, it corresponds to a reference value of leak current, any leak current above which may cause a skin burn. Thus, unless a leak current greater than the reference value occurs, the Schmidt circuit 26 produces no output. In this case, the switching transistors 27 and 31 are kept off, the relay coil 32 remains to be energized, and the relay switch 6 remains open. Under this condition, the resistor 4 alone is connected to the feedback circuit of the voltage amplifier 3, and the amplification factor of the voltage amplifier 3 is sufficiently large.

Suppose the wire 11 is cut off or the water impregnated in gauze (not shown) between the patient electrode 12 and the patient 13 evaporates, thereby degrading the electrical contact between the electrode 12 and the patient 13. Then the current may leak through, for example, the monitor electrodes of an electrocardiograph (not shown) or the metallic portion of an operation table (not shown). If this happens, the current flowing through the wire 9 does not varies so much, but the current flowing through the wire 11 is reduced. As a result, voltage $E_P$ at the secondary winding of the transformer 19 drops to make the current ratio $K (= E_P/E_A)$ less than 1. Thus, the output voltage of the division circuit 22 drops, and the output voltage of the inverter 25 elevates reversely.

If the output voltage of the inverter 25 surpasses the predetermined level, the Schmidt circuit 26 is triggered to produce an output. The output is then supplied to the base of the transistor 27, thereby turning on both transistors 27 and 31. Then, current flows through the relay coil 32 and closes the normally opened relay switch 6. As a result, the resistor 5 is connected in parallel to the resistor 4. Upon this connection, the amplification factor of the voltage amplifier 3 becomes smaller to reduce the current flowing from the wire 9 to the knife electrode 10. Consequently, the absolute amount of leak current is reduced, thus preventing an accident such as skin burn.

Since the division circuit 22 detects the voltage ratio K (i.e., ratio of the current $I_P$ flowing through the wire 11 to the current $I_A$ flowing through the wire 9). the Schmidt circuit 26 is triggered if K is smaller than the predetermined value, however small $I_A$ and $I_P$ are. When $I_A$ and $I_P$ are smaller than usual, skin burn would not occur even if such a current leak as mentioned above takes place. In this case, it is necessary to prohibit the switching transistors 27 and 31 from being turned on even if the Schmidt circuit 29 is triggered. To this end, a control circuit is provided.

The control circuit is constituted by the diode 28 and the Schmidt circuit 29. If the output voltage $E_A$ of the transformer 18 is as high as, or higher than the normal level, the Schmidt circuit 29 is triggered. In this case, the Schmidt circuit 29 produces a high level output, which is supplied to the cathode of the diode 28. Upon receipt of the high level output, the diode 28 is reversely biased and thus switched off. As a result, the switching transistors 27 and 31 operate solely in response to the output of the Schmidt circuit 26.

When the output voltage $E_A$ of the transformer 18 is lower than the normal level, the Schmidt circuit 29 is not triggered at all. Its output therefore drops to a low level. The low level output of the Schmidt circuit 29 is transferred through the diode 28 to the base of the transistor 27. Then, despite the output of the Schmidt circuit 26, the base of the transistor 27 is maintained at low level. Thus, even if the searing current happens to leak, the relay coil 32 does not effect any current control regardless of the voltage ratio $K (= E_P/E_A)$, so long as the searing current is smaller than usual and raises no fear of an accident such as skin burn.

In the embodiment shown in FIG. 1, the amplification factor of the voltage amplifier 3 is lowered to reduce the searing current when the relay coil 32 is energized. To warn a possible accident, a warning lamp or a warning buzzer may be provided so as to give forth an alarm when the relay coil 32 is energized.

Figure 3:
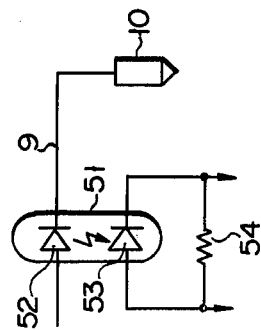
FIGS. 2 and 3 explain each a different arrangement for detecting the current flowing through the knife electrode of the embodiment illustrated in FIG. 1.
Figure 2:
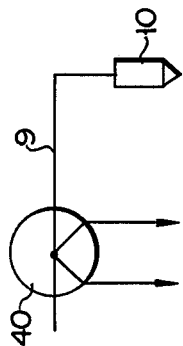

In the embodiment of FIG. 1, the current $I_A$ flowing through the knife electrode 10 and the current $I_P$ flowing through the patient electrode 12 are detected by the transformers 18 and 19, respectively. Instead, the current $I_A$ flowing through the wire 9 may be detected by such a thermocouple amperemeter 40 as shown in FIG. 2. Or, to detect the current $I_A$, a photocoupler 51 which is comprised of, as shown in FIG. 3, a light-emitting diode 52 and a photodiode 53 may be so arranged as to have the light-emitting diode 52 connected in the wire 9. The light-emitting diode 52 emits light the intensity of which depends on the current flowing through the wire 9. The photodiode 53 receives the light and converts the same into current. Thus, the searing current may be detected in the form of inter-terminal voltage of a resistor 54 which is connected in parallel to the photodiode 53.

What we claim is:

1. An electric knife device comprising a high frequency current source having first and second output terminals, a knife electrode connected to the first output terminal, a patient electrode connected to the second output terminal and to be electrically contacted with the patient, first current detector means for detecting the current flowing between the first output terminal and said knife electrode, second current detector means for detecting the current flowing between the second output terminal and said patient electrode, division circuit means for calculating the ratio between the outputs of said first and second current detector means and means fed by the output of said division circuit means for controlling the high frequency current flowing through said knife electrode in accordance with the ratio calculated by said division circuit means.

2. The electric knife device according to claim 1, wherein said high frequency current source comprises a high frequency oscillator, voltage amplifier means for amplifying the output of the high frequency oscillator, power amplifier means for amplifying the output of the voltage amplifier means, and a transformer having a primary winding connected to the output terminal of the power amplifier means and a secondary winding forming said first output terminal connected to said knife electrode and said second output terminal connected to said patient electrode and said current control means comprises a Schmidt circuit connected to said division circuit means and which is triggered when the output of said division circuit means becomes lower than a predetermined level, a transistor switching circuit connected to and turned on by the output of the Schmidt circuit, a relay coil connected to and energized when the transistor switching circuit is turned on, a normally opened relay switch connected to and closed when the relay coil is energized, and a resistor which is connected in feedback manner between the input and output terminals of said voltage amplifier means and serially to the normally opened relay switch so that when the relay switch is closed, the resistor is connected between the input and output terminals of said voltage amplifier means thereby to reduce the amplification factor thereof.

3. The electric knife device according to claim 2 further including a potentiometer connected to and receiving the output of said division circuit means and an analog inverter connected to and receiving the output of the potentiometer said inverter connected to and supplying an inversion output to said Schmidt circuit.

4. The electric knife device according to claim 1, wherein said first current detector means comprises a first wire connected between said first output terminal and said knife electrode, a first toroidal-shaped core through which the first wire passes, and a first coil wound about the first toroidal-shaped core, one terminal of said first coil being connected to the divisor input terminal of said division circuit means and the other terminal of said first coil being connected to a zero volt common; said second current detector means comprises a second wire connected between said second output terminal and said patient electrode, a second toroidal-shaped core through which the second wire passes, and a second coil wound about the second toroidal-shaped core, one terminal of said second coil being connected to the dividend input terminal of said division circuit means and the other terminal of said second coil being connected to said zero volt common.

5. The electric knife device according to claim 1, wherein said first current detector means includes a thermocouple amperemeter for detecting the current flowing between said first output terminal and said knife electrode.

6. The electric knife device according to claim 1, wherein said first current detector means includes a photocoupler for detecting the current flowing between said first output terminal and said knife electrode.

7. The electric knife device according to claim 1 further including a control circuit which is connected between the output terminal of said first current detector means and said current control means, said current control circuit including means for bringing said current control means into an inoperative state when the high frequency current flowing through said knife electrode is detected to be below a predetermined normal level.

8. The electric knife device according to claim 7, wherein said current control means comprises a first Schmidt circuit connected to and receiving the output of said division circuit means and triggered when the output of said division circuit means becomes lower than a predetermined level, a transistor switching circuit connected to and receiving the output of said first Schmidt circuit and which is turned on by the output of the first Schmidt circuit, a relay coil connected to and energized when the transistor switching circuit is turned on, and a normally opened relay switch connected to and closed when the relay coil is energized to reduce current flow to the knife electrode, said control circuit comprising a second Schmidt circuit connected to and receiving the output of said first current detector means and a diode connected between the output terminal of the second Schmidt circuit and the output terminal of said first Schmidt circuit to control current flow through the knife electrode.

* * * * *